(12) United States Patent
Lestoquoy

(10) Patent No.: US 10,206,754 B2
(45) Date of Patent: Feb. 19, 2019

(54) MODULAR SURGICAL DRAPE, ATTACHMENT FOR SURGICAL DRAPE AND RELATED MANUFACTURING PROCESS

(71) Applicant: Vygon, Ecouen (FR)

(72) Inventor: Patrick Lestoquoy, Attiches (FR)

(73) Assignee: Vygon (FR)

( * ) Notice: Subject to any disclaimer, the term of this patent is extended or adjusted under 35 U.S.C. 154(b) by 574 days.

(21) Appl. No.: 13/902,021

(22) Filed: May 24, 2013

(65) Prior Publication Data

US 2013/0312769 A1    Nov. 28, 2013

(30) Foreign Application Priority Data

May 25, 2012    (FR) .................................... 12 54870

(51) Int. Cl.
*A61B 19/08* (2006.01)
*A61B 46/00* (2016.01)

(52) U.S. Cl.
CPC .............. *A61B 46/40* (2016.02); *A61B 46/00* (2016.02); *Y10T 156/10* (2015.01); *Y10T 156/1052* (2015.01); *Y10T 428/24942* (2015.01)

(58) Field of Classification Search
CPC ....... A61B 19/08; A61B 19/088; A61B 46/20; A61B 2046/201; A61B 2046/205; A61B 2046/234; A61B 2046/236; A61B 46/23; Y10T 428/15
USPC .......................................................... 128/849
See application file for complete search history.

(56) References Cited

U.S. PATENT DOCUMENTS

| 3,905,369 A | * | 9/1975 | Kyte | ...................... A61F 13/58 |
| | | | | 156/66 |
| 4,600,001 A | | 7/1986 | Gilman | |
| 4,600,801 A | | 7/1986 | Guha et al. | |
| 4,917,924 A | * | 4/1990 | Huang | ............... A22C 13/0003 |
| | | | | 138/118.1 |
| 5,468,231 A | * | 11/1995 | Newman | ............... A61M 25/02 |
| | | | | 128/DIG. 26 |

(Continued)

FOREIGN PATENT DOCUMENTS

| WO | 9707760 A1 | 3/1997 |
| WO | 2005007020 A2 | 1/2005 |

OTHER PUBLICATIONS

Assnsurgtech: "Surgical Positioning, Prepping and Draping DVD sample clip", upload date Jul. 30, 2009 (Jul. 30, 2009), XP055052031, youtube.com. Retrieved from the Internet: <URL: http://www.youtube.comjwatch?v=VB1ufcUCr6c>.

(Continued)

*Primary Examiner* — Kari K Rodriquez
*Assistant Examiner* — Camtu T Nguyen
(74) *Attorney, Agent, or Firm* — Lerner, David, Littenberg, Krumholz & Mentlik, LLP

(57) ABSTRACT

The invention relates to a surgical drape (1) comprising a main sheet (10), characterized in that it comprises a drape attachment (20) composed of:
  a separable film (22) having at least one internal layer (22*a*) and one external layer (22*b*), the internal layer (22*a*) having less mechanical resistance than the external layer (22*b*), and
  a layer of adhesive (24), fixed to the internal layer (22*a*) of the separable film (22),
  the drape attachment being fixed to the main sheet (10) by means of the layer of adhesive (24).

18 Claims, 2 Drawing Sheets

(56) References Cited

U.S. PATENT DOCUMENTS

| | | | |
|---|---|---|---|
| 5,611,356 A * | 3/1997 | Rothrum | A61B 46/00 128/844 |
| 6,302,867 B1 | 10/2001 | Brown, Jr. et al. | |
| 9,216,254 B2 * | 12/2015 | Taylor | A61M 5/321 |
| 2005/0284487 A1 * | 12/2005 | Gellerstedt | A61B 46/00 128/849 |
| 2009/0145539 A1 * | 6/2009 | Kreckel | A47G 1/175 156/247 |
| 2010/0031966 A1 * | 2/2010 | Allen | A61B 46/00 128/851 |
| 2010/0186754 A1 * | 7/2010 | Carrez | A61B 46/00 128/853 |
| 2012/0245549 A1 * | 9/2012 | Sakaguchi | A61F 13/15585 604/385.27 |

OTHER PUBLICATIONS

French Preliminary Search Report for Application No. FR1254870 dated Feb. 1, 2013.

* cited by examiner

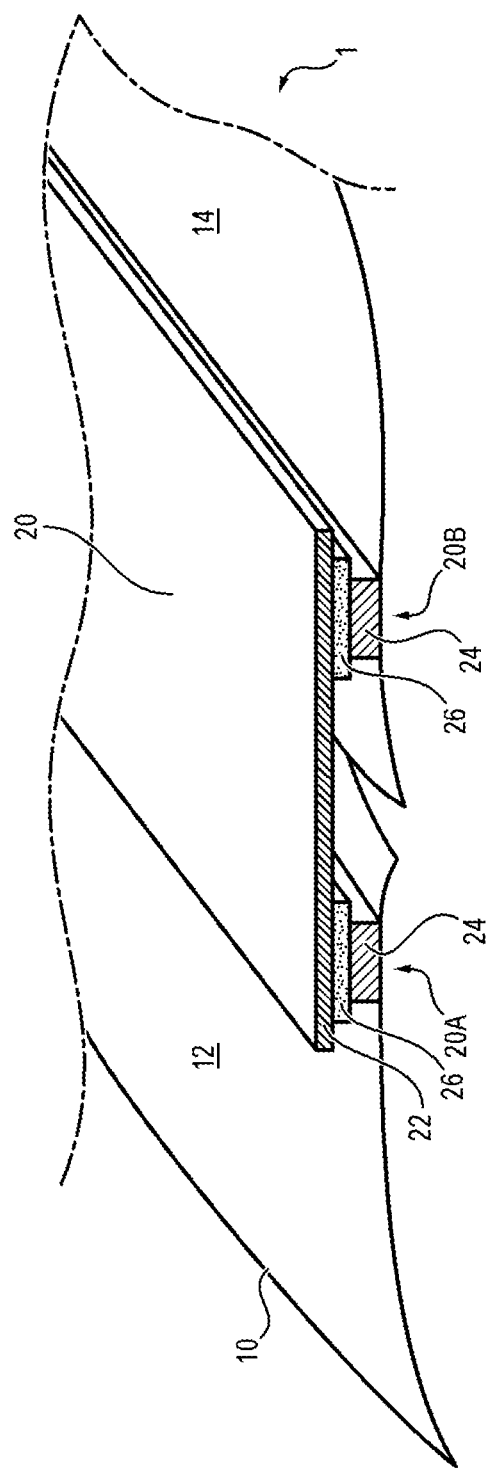

MODULAR SURGICAL DRAPE, ATTACHMENT FOR SURGICAL DRAPE AND RELATED MANUFACTURING PROCESS

CROSS-REFERENCE TO RELATED APPLICATIONS

The present application claims priority from French Patent No. 1254870 filed May 25, 2012, the disclosure of which is hereby incorporated herein by reference.

BACKGROUND OF THE INVENTION

The invention relates in general to surgical drapes and their manufacturing processes.

More precisely, the invention relates to separable surgical drapes and/or those comprising a removable drape element.

PRIOR ART

Such surgical drapes are already known.

For example, there are surgical drapes comprising a window through which a surgeon can access a surgical drape to introduce into the body an instrument such as a tube or a wire optionally extended by a line which must stay in place while the drape must be removed. To remove the drape despite the presence of instruments entering via the window, it is known to cut the drape away using a cutting tool or tear it to open the drape laterally. But these operations complicate the work of the surgeon and constitute a risk for the instruments and for the patient.

To make these operations easier, it has been proposed to provide the drape with tear lines or cutting or tearing lines, as described for example in documents EP 1 009 318 and WO 99/16377. However, only to a limited extent do these measures make cutting of the drape easier and they do not sufficiently resist penetration by liquids, possibly introducing asepsis and infections.

Patent application WO 2007/083032 therefore proposes a surgical drape comprising two parts of a sheet held in extension of each other by an impermeable adhesive ribbon. The resulting drape resists penetration from liquids and can be peeled off by the surgeon when he wants to open the drape without removing the instruments in place.

Using such a ribbon makes the join between the drapes impermeable to liquids and resists current liquid penetration tests based on water columns. However, the peeling of the ribbon adhesive by the surgeon leaves sticky residue on the drape, which can hamper the surgeon during surgery. The adhesive can be transferred to the catheter in place during surgery, with the risk it might be extracted accidentally. The catheter would then have to be replaced, and this can be dangerous for the patient.

Document WO 2009/010509 as such proposes a surgical drape comprising two impermeable peelable films whereof two edges are jointed. The films are held together by an impermeable peelable narrow ribbon via thermal welding for later separating the films and the strip by peeling. The film and the ribbon are formed from two sheets of superposed polyethylene (PE), one of which is made of very low-density polyethylene (LDPE). Thermal welding is done such that the LDPE sheet of the films is in contact with the PE sheet of the ribbon. As a variant, thermal welding is done while the LDPE sheet of the films is in contact with the LDPE sheet of the ribbon. Thermal welding fuses the LDPE sheets which stick together, and during peeling their very low mechanical resistance enables the surgical drape to be opened by a surgeon.

The resulting surgical drapes are impermeable and resist penetration by liquids during use.

However, their manufacturing process can pose difficulties. For example, welding the narrow ribbon on the counterpart parts of the surgical drape needs very precise handling and gestures, causing losses and investment in welding equipment. Making the drape wholly or partly from separable film is also costly due to the price of the raw material used. When the drape comprises several different materials, for example when it comprises a transparent window made of polyethylene (PE) framed by a non-woven sheet, welding the ribbon is delicate due to the changes in thickness and the passage from one material to another.

Thermal welding of the parts of the surgical drape by means of the peelable ribbon has therefore a high retail cost in terms of materials and manufacturing process and can be impossible depending on the materials used (especially in the case of surgical drapes formed in materials which are not thermally weldable).

Finally, document EP 2 364 667 describes a surgical drape, especially for childbirth, comprising a detachable pocket fixed to the drape by thermosealing of a multilayer peelable film made of polyethylene. In this way, after filling of the drainage bag, the latter is removed from the drape by tearing of the lower layer of the separable film.

SUMMARY OF THE INVENTION

An aim of the invention is to propose a modular surgical drape, adapted when needed to be separated into two parts without the aid of a cutting instrument, while ensuring impermeability and without weakening, which is also simple to produce, of moderate cost and is adapted for manufacture online, irrespective of its constituent materials.

Another aim of the invention is to propose a surgical drape capable of detachably receiving a separate drape element, rapidly and safely.

For this, the invention proposes a surgical drape comprising a main sheet, characterised in that it comprises a drape attachment comprising:

a separable multilayer film having at least one internal layer and one external layer, the internal layer having less mechanical resistance than the external layer such that the internal layer breaks or tears before the external layer during traction force exerted on the multilayer film, and a layer of adhesive fixed to the internal layer of the separable multilayer film, the drape attachment being fixed to the main sheet by means of the layer of adhesive.

Other optional and non-limiting characteristics of the surgical drape are the following:

internal cohesion of the internal layer is weaker than internal cohesion of the external layer;

the internal layer is finer than the external layer;

it also comprises a support layer welded onto the internal layer of the separable film, to which the layer of adhesive is fixed;

the internal layer of the separable film comprises at least one of the following materials: low-density polyethylene (LDPE), very low-density polyethylene (VLDPE), polyethylene/ethyl vinyl acetate (PE/EVA) and the external layer comprises at least one of the following materials: polyethylene (PE), polyamide (PA), poly(ethylene terephthalate) (PET).

the attachment further comprising an additional layer of adhesive (28) fixed to the separable film, to the side opposite the external layer;

the additional layer of adhesive is covered by a peelable protective sheet;

the main sheet is divided into two sheet parts which are held in extension of each other by the drape attachment (20) to form the main sheet of said drape; and the layer of adhesive is applied locally in two distinct and separate zones of the separable film, and the drape attachment is fixed to the sheet parts of the main sheet such that each of said zones is fixed to one of the sheet parts.

According to a second aspect, the invention also relates to an attachment for a surgical drape as described hereinabove, which comprises a separable multilayer film having at least one internal layer and one external layer, the internal layer having less mechanical resistance than the external layer such that the internal layer breaks or tears before the external layer during traction force exerted on the multilayer film, and a layer of adhesive fixed to the internal layer of the separable film.

Other optional and non-limiting characteristics of the surgical drape are the following:

it further comprises a protective sheet adapted to cover the layer of adhesive; and the layer of adhesive is applied locally in two distinct and separate zones of the separable film.

According to a third aspect, the invention also proposes a manufacturing process of a surgical drape as described hereinabove, comprising the following steps:

producing the drape attachment, and fixing the layer of adhesive of the drape attachment onto the surgical drape.

In a non-limiting manner, the layer of adhesive can be applied in two distinct and separate zones of the separable film during manufacture of the drape attachment, and the process can further comprise, after the fastening step of the drape attachment on said surgical drape, a cutting step of the main sheet of the surgical drape into two sheet parts held in extension of each other by the drape attachment.

BRIEF DESCRIPTION OF THE DRAWINGS

Other characteristics, aims and advantages of the invention will be more clearly understood from the following detailed description, given in reference to the attached figures given by way of non-limiting examples, in which:

FIG. 4 illustrates an embodiment of a surgical drape according to the invention.

DETAILED DESCRIPTION

Figure 1:
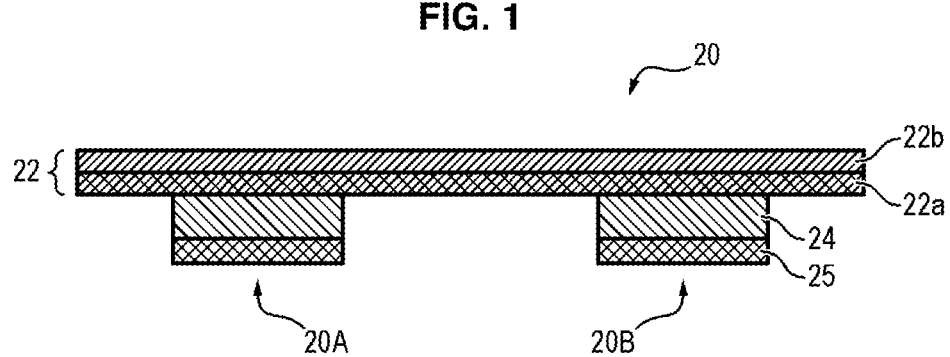
FIG. 1 illustrates a first embodiment of an attachment of a surgical drape according to the invention.
Figure 2:
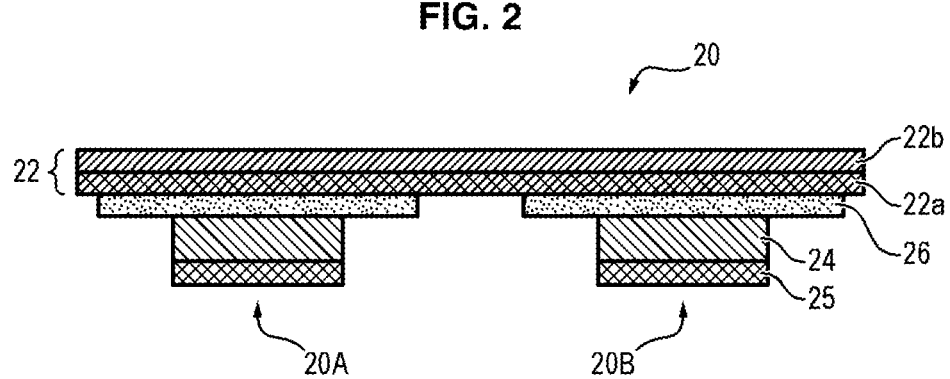
FIG. 2 illustrates a second embodiment of an attachment of a surgical drape according to the invention.
Figure 3:
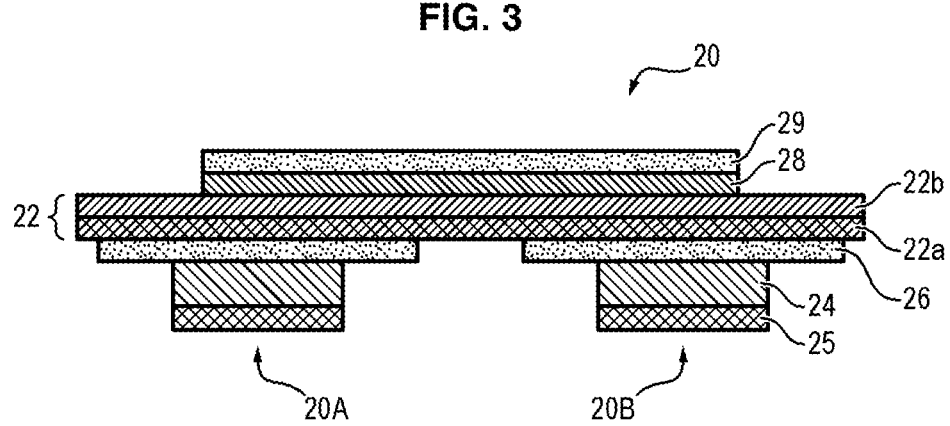
FIG. 3 illustrates a third embodiment of an attachment of a surgical drape according to the invention.

A surgical drape 1 according to the present invention comprises a main sheet 10, on which is fixed an attachment of a surgical drape 20. The attachment 20 is adapted to keep together two drape parts 12, 14 in extension of each other so as to form the main sheet 10, and/or detachably fix a drape element.

The drape attachment 20 can be attached to the surgical drape 1 during its manufacture.

It comprises a separable film 22, on which is fixed a layer of adhesive 24.

The separable film 22 can for example comprise a multilayer film, comprising at least one internal layer 22a intended to receive the layer of adhesive 24, and an external layer 22b. The multilayer film 22 can for example be obtained by coextrusion of its layers.

The internal layer 22a is adapted to be torn by a surgeon wanting to remove the drape attachment 20. More precisely, the internal layer 22a has less mechanical resistance in traction than the external layer 22b, such that it breaks or tears before the external layer 22b during traction force exerted on the multilayer film 22 in a direction normal to the direction of extension of said layers, the external layer 22b remaining intact or undergoing only slight internal delamination. For this, the internal layer 22a can be made of material having less internal cohesion than the internal cohesion of the external layer 22b, and/or have less thickness (in the direction normal to the plane of the layers).

For example, for an external layer 22b made of polyethylene (PE), the internal layer 22a can especially comprise low-density polyethylene (LDPE), very low-density polyethylene (VLDPE), polyethylene/Ethyl Vinyl Acetate (PE/EVA), or any other adapted tearable material having low internal cohesion.

As a variant, the external layer can be made of polyamide (PA) or poly(ethylene terephthalate) (PET), or any other polymer adapted for creating surgical drapes.

The separable film 22 can further comprise other layers, as per the preferred mechanical properties. For example, the separable film 22 can comprise one or more layers in addition to the internal and external layers, having greater mechanical resistance than the internal layer 22a, and made for example of polyethylene (PE).

Optionally, the separable film 22 can be symmetrical so that it can be used in any direction without risking the layer of adhesive sticking on a layer having excessive mechanical resistance, limiting potential manufacturing errors of the surgical drape 1. For example, the separable film 22 can comprise an internal layer 22a made of material of low mechanical cohesion included in the list hereinabove, one or more external layers fixed onto the internal layer 22a, comprising for example PE, and an upper covering layer identical to the internal layer 22a, arranged on the external layers.

The layer of adhesive 24 is selected so as to exhibit greater resistance to peeling than the mechanical resistance of the internal layer 22a of the separable film 22, such that when traction force is applied to the attachment 20, the internal layer 22a of the separable film breaks before the adhesive unsticks. In fact, rupturing between the surgical drape 1 and the attachment 20 should occur at the level of the internal layer 22a of the separable film 22, and not of the layer of adhesive 24 or of the surgical drape 1, so as to overcome the abovementioned drawbacks of the prior art. For example, the layer of adhesive 24 has mechanical resistance of at least two Newtons for a one-inch thickness (corresponding to around 2.54 cm). This point will be detailed more hereinbelow in this description.

Also, the layer of adhesive 24 should be adapted to be fixed directly or indirectly on the internal layer 22a of the separable film 22. In this way, the layer of adhesive 24 can be fixed directly onto the internal layer 22a, or by way of a support layer 26.

For example, the layer of adhesive 24 can be fixed to a sheet of polyethylene, the sheet of polyethylene 26 then being welded to the internal layer 22a of the separable film 22. This embodiment has the advantage of attaching the layer of adhesive 24 previously fixed to the sheet of polyethylene then simply welding the sheet of polyethylene to the internal layer 22a of the separable film 22. A pressure-sensitive adhesive type (PSA) could especially be used.

The resulting drape attachment 20 can then be fixed to a surgical drape 1, then peeled manually by a surgeon when the latter deems it necessary. During peeling, the drape attachment 20 breaks at the level of its internal layer 22a, leaving the layer of adhesive 24 covered by part of the internal layer 22a on the drape (and when needed of the support layer 26), such that the surgical drape 1 does not stick.

According to a preferred embodiment, the surgical drape 1 is made of non-absorbent material to limit the risk of infection at the level of the interface between the drape attachment 20 and the surgical drape 1.

An example of manufacturing a separable drape will now be described.

During a first step, a drape attachment 20 is manufactured. Advantageously, the drape attachment 20 can be made automatically by an adapted installation, by stacking and joining together the separable film 22 and the layer of adhesive 24 by means or not of the support layer 26, the different elements being taken from as many rollers. It is possible to make coils or long strips of drape attachment 20 rapidly and economically, which can be stored before being fixed to the drape 1.

In the case of manufacturing a separable drape, the layer of adhesive 24 and when needed the support layer 26 are applied in two separate and distinct zones 20A, 20B of the internal layer 22a of the separable film 22, for example according to two substantially parallel strips.

The resulting drape attachments 20 can be stored and/or transported prior to use. For this purpose, it is possible to cover the free surface of the adhesive layers with a protective sheet 25, for example a siliconised paper. The protective sheet 25 avoids the risk of damaging the layers of adhesive, and their premature adhesion. The protective sheet 25 must be removed before the attachment 20 is attached to the drape 1.

By way of variant, the layer of adhesive 24 can be activated, for example by pressure, by application of ultraviolet, heat, etc. and therefore adheres only after activation.

The drape attachment 20 is then brought to a main sheet 10 of a mono- or multi-material surgical drape 1, and fixed to the latter in the preferred place. For example, the attachment 20 can extend from one edge to the other of the main sheet 10, so as to separate it into two distinct parts 12, 14. As a variant, the attachment 20 can extend over one part only of the length of the main sheet 10.

The main sheet 10 of the drape can then be cut off between the distinct and separate zones of the drape attachment 20, for example manually by means of scissors or automatically using a blade, to separate the main sheet 10 into two sheet parts 12, 14 without damaging the separable film 22. The presence of the separable film 22 prevents penetration by liquids through the drape 1, in spite of separation of the main sheet 10 into two sheet parts, at the same time enabling the two sheet parts 12, 14 to be separated following peeling of the attachment 20.

By way of variant, the main sheet 10 can comprise two distinct sheet parts 12, 14 prior to fastening of the drape attachment 20, either because the main sheet 10 has been cut off previously, or because the sheet parts 12, 14 have been made separately. The sheet parts 12, 14 are positioned opposite, then the drape attachment 20 is fixed to the latter such that each sheet part 12, 14 is fixed to one of the zones 20A, 20B of the attachment 20.

In all cases, using an attachment 20 according to the invention joins together the drape parts irrespective of their respective materials simply, rapidly and effectively. No welding step is necessary, merely applying the adhesive to the drape part to be made separable must be carried out.

Also, drape attachments 20 can be made online on an adapted machine, by superposition and fastening of the separable film 22, the layer of adhesive 24 and any support 26 and protective 25 layers. By way of variant, all the layers forming the separable film 22 and the layer of adhesive 24 can be coextruded, then superposed and fixed to the support 26 and protective 25 layers.

Only the fastening step of the drape attachment 20 is therefore made separately, either manually or by an adapted machine. This step, rapid and simple to do, consists simply of removing any protective sheet 25, sticking the attachment onto a drape sheet then cutting off the surgical drape 1 below the drape attachment 20. The manufacturing process of peelable drapes is therefore semi-automated, which boosts production rate and limits material and handling costs.

The drape attachment 20 can also be used to fix a removable drape element, such as a drainage bag.

For this, the drape attachment 20 also comprises, at the level of its external face, corresponding to the external layer 22b of the separable film 22, an extra strip of adhesive 28. This extra strip of adhesive 28 can be covered by a protective sheet 29, such as siliconised paper, when the drape element is not fixed to the surgical drape 1 at the time of its manufacture, but later on.

The removable element can be fixed to the extra strip of adhesive 28 after any protective sheet 29 is removed, while the internal face of the attachment 20 is fixed to the main sheet 10 of the surgical drape 1.

The extra strip of adhesive 28 is selected so that it is capable of supporting the load of the removable drape element without breaking, and has greater mechanical resistance than that of the internal layer 22a of the separable film 22 to ensure that breaking of the attachment 20 during peeling of the drape element occurs at the level of the internal layer 22a so as not to leave traces of adhesive on the drape 1. For example, the extra 28 layer of adhesive 24 can be identical to the layer of adhesive 24 fixed to the internal layer 22a.

Of course, the attachment can be fixed to the surgical drape 1 before or after fixing to the removable element.

When the surgeon wants to remove the removable element, all he has to do is peel off the attachment 20 by pulling on the element. The drape attachment 20 breaks and separates at the level of the internal layer 22a of the separable film 22, leaving the layer of adhesive 24 (when needed fitted with the support layer 26) and part of the internal layer 22a on the surgical drape 1, the rest staying attached to the removable element.

In this embodiment, the drape attachment 20 can comprise a single zone fitted with adhesives.

In a variant embodiment, the drape attachment 20 can make the drape separable and detachably fix a drape element at the same time, the layer of adhesive 24 on the internal layer 22a side being divided into two distinct and separate zones, each of the zones being provided to hold two sheet parts 12, 14 in extension of each other.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An operating drape comprising:
   a main sheet; and
   a drape attachment, wherein the drape attachment comprises:
      a separable multilayer film having at least one internal layer and an external layer, the at least one internal layer having lower mechanical resistance than that of the external layer such that the at least one internal layer breaks or tears before the external layer during traction force exerted on the separable multilayer film, wherein internal cohesion of the at least one internal layer is less than internal cohesion of the external layer, the material of the at least one internal layer being distinct from the material of the external layer, and
      a layer of adhesive fixed to the at least one internal layer of the separable multilayer film, the drape attachment being fixable to the main sheet by the layer of adhesive,
      wherein the layer of adhesive has a greater mechanical resistance to peeling than that of the at least one internal layer of the separable multilayer film, such that when traction force is applied to the drape attachment, the at least one internal layer of the separable multilayer film breaks or tears before the layer of adhesive unsticks from the main sheet or the drape attachment.

2. The operating drape of claim 1, wherein the layer of adhesive is a pressure-sensitive adhesive.

3. The operating drape of claim 1, wherein the mechanical resistance of the layer of adhesive is at least two Newtons for a one-inch thickness.

4. The operating drape of claim 1, further comprising a support layer between the layer of adhesive and the at least one internal layer of the separable multilayer film, wherein the support layer is welded onto the at least one internal layer of the separable multilayer film, and wherein the layer of adhesive is directly fixed to the support layer and indirectly fixed to the at least one internal layer of the separable multilayer film.

5. The operating drape of claim 1, in which the at least one internal layer of the separable multilayer film comprises at least one of the following materials: low-density polyethylene (LDPE), very low-density polyethylene (VLDPE), polyethylene/ethyl vinyl acetate (PE/EVA).

6. The operating drape of claim 1, in which the external layer comprises at least one of the following materials: polyethylene (PE) polyamide (PA), poly(ethylene terephthalate) (PET).

7. The operating drape of claim 1, in which the drape attachment further comprises an additional layer of adhesive fixed to an outer surface of the external layer of the separable multilayer film, wherein an inner surface of the external layer is fixed to the at least one internal layer.

8. The operating drape of claim 7, in which the additional layer of adhesive is covered by a peelable protective sheet.

9. The operating drape of claim 1, wherein the main sheet is divided into two sheet parts which are held in extension of each other by the drape attachment so as to form the main sheet.

10. The operating drape of claim 9, in which the layer of adhesive is applied locally in two distinct and separate zones of the separable multilayer film, and the drape attachment is fixed to the sheet parts of the main sheet such that each of said two distinct and separate zones is fixed to one of the sheet parts.

11. A manufacturing process of an operating drape according to claim 1, comprising the following steps:
    making the drape attachment, and
    fixing the layer of adhesive of the drape attachment on the operating drape.

12. The manufacturing process according to claim 11, in which the layer of adhesive is applied in two distinct and separate zones of the separable multilayer film during manufacture of the drape attachment, and the process also comprises, after the fastening step of the drape attachment on said operating drape, a cutting step of the main sheet of the operating drape along a direction of extension of the drape attachment, so as to split the main sheet into two sheet parts held in extension of each other by the drape attachment.

13. The operating drape of claim 1, wherein the drape attachment extends longitudinally in a direction so as to hold two parts of the main sheet in extension of each other along said direction.

14. An attachment for an operating drape, the attachment comprising:
    a separable multilayer film extending longitudinally in a direction, having at least one internal layer and one external layer, the at least one internal layer having less mechanical resistance than that of the external layer such that the at least one internal layer breaks or tears before the external layer during traction force exerted on the separable multilayer film, wherein internal cohesion of the at least one internal layer is less than internal cohesion of the external layer the material of the at least one internal layer being distinct from the material of the external layer, and
    a layer of adhesive extending longitudinally in said direction, fixed to the at least one internal layer of the separable multilayer film,
    wherein the layer of adhesive has a greater mechanical resistance to peeling than that of the at least one internal layer of the separable multilayer film, such that when traction force is applied to the attachment, the at least one internal layer of the separable multilayer film breaks or tears before the layer of adhesive unsticks from the attachment.

15. The attachment for an operating drape of claim 14, further comprising a protective sheet adapted to cover the layer of adhesive.

16. The attachment for an operating drape of claim 14, in which the layer of adhesive is applied locally in two distinct and separate zones of the separable multilayer film.

17. The attachment for an operating drape of claim 14, wherein the layer of adhesive is a pressure-sensitive adhesive.

18. The attachment for an operating drape of claim 14, wherein the mechanical resistance of the layer of adhesive is at least two Newtons for a one-inch thickness.

* * * * *